United States Patent [19]

Van Poucke et al.

[11] 3,930,861

[45] Jan. 6, 1976

[54] SILVER HALIDE EMULSIONS CONTAINING 3-ANILINO-2-PYRAZOLIN-5-ONE COLOR COUPLERS

[75] Inventors: Raphael Karel Van Poucke, Berchem; Hector Alfons Vanden Eynde, Edegem; Leo August Van Wijnsberghe, Gravenwezel, all of Belgium

[73] Assignee: Agfa-Gevaert N.V., Mortsel, Belgium

[22] Filed: Mar. 18, 1974

[21] Appl. No.: 452,325

[30] Foreign Application Priority Data
Apr. 6, 1973 United Kingdom............... 16626/73

[52] U.S. Cl. .................... 96/56.5; 96/56.6; 96/100; 260/310 C

[51] Int. Cl.² ...................... G03C 7/00; G03C 1/40
[58] Field of Search..................... 96/100, 56.5, 56.6

[56] References Cited
UNITED STATES PATENTS

| | | | |
|---|---|---|---|
| 2,289,805 | 7/1942 | Porter et al. | 96/100 |
| 2,343,703 | 3/1944 | Porter et al. | 96/100 |
| 3,415,652 | 12/1968 | Porter | 96/100 |
| 3,798,234 | 3/1974 | Meier et al. | 96/100 |

*Primary Examiner*—J. Travis Brown
*Attorney, Agent, or Firm*—A. W. Breiner

[57] ABSTRACT

Novel magenta-forming 3-anilino-2-pyrazolin-5-one colour couplers for use in silver halide photography are described wherein the anilino group carries an aryloxysulphonyl group.

10 Claims, No Drawings

SILVER HALIDE EMULSIONS CONTAINING 3-ANILINO-2-PYRAZOLIN-5-ONE COLOR COUPLERS

The present invention relates to 2-pyrazolin-5-one colour couplers, to the preparation thereof, to photographic silver halide elements and developing compositions containing such colour couplers as well as to colour development processes wherein said colour couplers take part in the formation of a magenta dye image.

It is known that for the formation of a photographic colour image in a light-sensitive silver halide emulsion layer the exposed silver halide is developed by means of an aromatic primary amino colour developer in the presence of a colour coupler which by reaction with the oxidized developer forms a dye on the areas corresponding to the silver image.

In subtractive three-colour photography it is common practice to use a photographic element comprising at least one red-sensitized, green-sensitized and blue-sensitive silver halide emulsion layer, wherein upon development in the presence of suitable colour couplers, cyan, magenta and yellow dye images are formed respectively.

It is desirable that colour couplers employed in colour photography have good coupling activity, and produce dye images that have the desired spectral absorption characteristics and favourable stability against light, moisture and heat.

The colour couplers may be of the diffusible type or of the non-diffusible type. By diffusible couplers is meant colour couplers the dispersability or solubility of which is sufficient to enable them to be usefully incorporated in aqueous colour developing solutions whereas by non-diffusible colour couplers is meant colour couplers intended for use in the photographic element where they should remain during colour development. Non-diffusible colour couplers are usually obtained by providing in the colour coupler molecule one or more ballasting groups which are sufficiently large to prevent diffusion of the colour coupler e.g. aliphatic groups of 5 to 20 C-atoms.

It is known that for homogeneously distributing non-diffusible colour couplers in a hydrophilic colloid layer, more particularly a silver halide emulsion layer, special techniques are to be used. Colour couplers containing a water-solubilizing group e.g. a sulpho group can be incorporated in the hydrophilic colloid compositions from alkaline solutions if necessary in the presence of a water-miscible solvent e.g. ethanol. Water-insoluble or sparingly watersoluble colour couplers can be incorporated in hydrophilic colloid compositions by dispersing techniques using highboiling water-immiscible solvents e.g. tricresyl phosphate and dibutylphthalate and/or low boiling water-immiscible solvents e.g. methylene chloride, ethyl acetate, diethyl carbonate, etc. No matter what technique is used, the colour couplers should be homogeneously distributed in the hydrophilic colloid layer and have high stability against crystallization so that colour image formation is not impaired.

For the formation of the magent a separation image it is known to use 2-pyrazolin-5-one colour couplers. These colour couplers may comprise in the 1-position an alkyl or substituted alkyl group e.g. alkyl with 1 to 22 C-atoms, haloalkyl e.g. chloro and fluoroalkyl, cyanoalkyl, e.g. β-cyanoethyl, benzyl, etc., an aryl or substituted aryl group e.g. phenyl, 2-chlorophenyl, 2,6-dichlorophenyl, 2,4,6-trichlorophenyl, 2,4-dichloro-6-methylphenyl, 2-chloro-4,6-dimethylphenyl, cyanophenyl, alkoxyphenyl, alkylthiophenyl, alkylsulphonylphenyl, sulphamoyl- or carbamoylphenyl etc. or a heterocycle e.g. 2-thiazolyl, 2-benzothiazolyl, 2-imidazolyl, 2-benzimidazolyl, 2-oxazolyl, 2-benzoxazolyl, etc.

In the 3-position of 2-pyrazolin-5-one colour couplers, there is usually an alkylamino group, an arylamino group, an acylamino group, an acyloxyamino group or an ureido group.

In accordance with the present invention novel 2-pyrazolin-5-one colour couplers comprising in the 3-position an anilino group are provided which yield upon colour development azomethine dyes having favourable sensitometric and spectral properties with high transmission for blue and red light and favourable stability against light, heat and moisture. Moreover, the non-diffusible types of these colour couplers lend themselves very well for being incorporated in hydrophilic colloid compositions more particularly a light-sensitive silver halide emulsion by means of dispersion techniques and stable, finely divided dispersions of the colour couplers in the emulsion layers can be obtained in this way.

The 3-anilino-2-pyrazolin-5-one colour couplers according to the present invention are characterized in that the anilino group carries an aryloxysulphonyl group including a substituted aryloxysulphonyl group. The aryloxysulphonyl group has a high stability against hydrolysis contrary to alkoxysulphonyl groups which as is known from British Patent 843,940 are hydrolytically unstable.

More particularly, the 3-anilino-2-pyrazolin-5-one colour couplers according to the present invention can be represented by the formula:

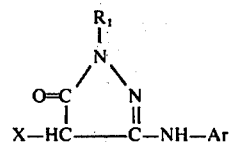

wherein:

$R_1$ represents alkyl including substituted alkyl e.g. benzyl, substituted benzyl e.g. chlorobenzyl, cyanoalkyl, e.g. 2-cyanoethyl, fluoroalkyl e.g. 2,2,2-trifluoroethyl, aryl including substituted aryl e.g. aryl substituted with one or more alkyl, alkoxy, alkylthio, phenoxy, halogen, alkylsulphonyl, carbalkoxy, fluorosulphonyl, trifluoromethyl, sulphamoyl, carbamoyl, cyano or nitro groups, or a heterocycle, X represents hydrogen or a substituent that exhibits two-equivalent character on colour development e.g. a halogen atom e.g. chlorine atom, an alkylthio, arylthio, or heterocyclic thio group, an alkoxy, aryloxy or acyloxy group, a sulpho group or an arylazo group, Ar represents a phenyl group or substituted phenyl group carrying an aryloxysulphonyl group e.g. a phenyloxysulphonyl group which may be substituted e.g. with one or more alkyl, cycloalkyl, hydroxy, halogen, alkoxy, alkylthio or alkylsulphonyl groups; more particularly Ar represents a group of the formule:

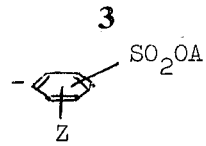

wherein:

Z is hydrogen, halogen, alkoxy, alkylthio, etc., and A is a carbocyclic aryl group e.g. phenyl which may be substituted e.g. with one or more of the groups alkyl, cycloalkyl, hydroxy, halogen, alkoxy, alkylthio or alkylsulphonyl.

The term "two-equivalent character" as applied to colour coupling systems is well known and is described for example in "The theory of the photographic process", C.E.K. Mees, The Mac Millan Company, New York, 1966, p.390. It means that by the presence of the splittable substituent on the active methylene group only two equivalents of silver are required for the formation of the dye contrary to four equivalents when the methylene group is not substituted.

The colour couplers for magenta according to the present invention can be of the diffusible- or non-diffusible type as described above. The invention is particularly concerned with non-diffusible colour couplers for use in the photographic colour element itself. For this purpose the colour couplers can be provided in the substituents on the 1- or 3-positions of the pyrazolon nucleus with one or more ballasting groups comprising an aliphatic straight-chain or branched-chain hydrocarbon group of at least 5 C-atoms. The ballasting group(s) rendering the colour coupler fast to diffusion in hydrophilic colloid layers is preferably a substituent on the aryloxysulphonyl group or a substituent on a 1-aryl group. These non-diffusible colour couplers of the invention lend themselves very well for being incorporated in the silver halide emulsion by dispersing techniques.

The present invention provides besides novel 2-pyrazolin-5-one compounds, a method of producing a magenta coloured photographic image in a photographic light-sensitive silver halide material which comprises exposing the material and developing it with an aromatic primary amino colour developing agent in the presence of a 2-pyrazolin-5-one colour coupler as defined above.

The present invention further provides a photographic element containing at least one silver halide emulsion layer and a 2-pyrazolin-5-one colour coupler as defined above comprising in its molecule one or more aliphatic hydrocarbon groups of at least 5 C-atoms.

The colour couplers of the present invention can be prepared according to methods known in the art. For example, they can be prepared by reaction of the known alkyl or aryl hydrazines with an aryloxysulphonylaniline and ethyl $\beta,\beta,\beta$-trimethoxypropionate according to the method described in the published German Pat. No. 2,042,920.

The aryloxysulphonylanilines can be prepared by means of one of the following procedures :

1. reaction of a nitrobenzene sulphochloride with phenol or naphthol in pyridine followed by catalytic hydrogenation;

2. reaction of an acetylaminobenzene sulphochloride with a phenol or naphthol in pyridine followed by deacetylation, and 3. reaction of a nitrobenzene sulphochloride with the sodium salt of a phenol or naphthol in benzene followed by catalytic hydrogenation.

Representative aryloxysulphonylanilines prepared according to one of the above procedures and useful for the preparation of the colour couplers of the invention are listed in the following Table I.

Table I

| | Amine compound | Procedure | Melting point °C |
|---|---|---|---|
| 1. | $H_2N-\langle\rangle-SO_2O-\langle\rangle-C_5H_{11}-i$ (with $i-C_5H_{11}$ substituent) | 1 | 106 |
| 2. | $H_2N-\langle\rangle-SO_2O-\langle\rangle-C(CH_3)_3$ (with H substituent) | 1 | 119 |
| 3. | $H_2N-\langle\rangle-SO_2O-\langle\rangle-OH$ (with $C(CH_3)_3$ substituent) | 1 | 165 |
| 4. | $H_2N-\langle\rangle$ (with $OCH_3$); $SO_2O-\langle\rangle-C(CH_3)_3$ (with H substituent) | 2 | 103 |

Table I—Continued
| | Amine compound | Procedure | Melting point °C |
|---|---|---|---|
| 5. | 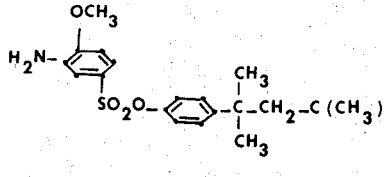 | 2 | 98 |
| 6. | 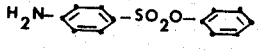 | 1 | 146 |
| 7. | 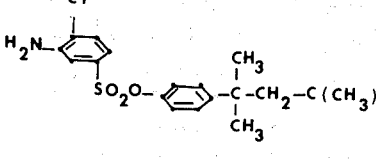 | 3 | 105 |
| 8. | 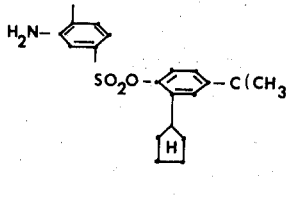 | 3 | 101 |
| 9. |  | 1 | 73 |
| 10. | 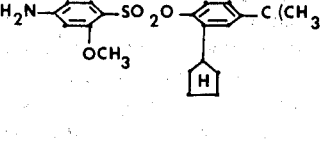 | 1 | 113 |
| 11. | 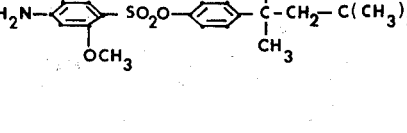 | 1 | 146 |
| 12. | 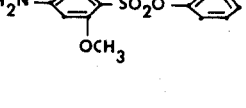 | 1 | 138 |
| 13. | 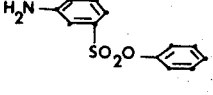 | 2 | 63 |

The following preparations illustrate how the colour couplers of the invention can be prepared. Representative examples of colour couplers are listed in table II hereinafter.

Preparation 1

Colour coupler 1 of table II 38.9 g (0.1 mole) of amine (1) in 100 ml of acetic acid were stirred for 90 min. at room temperature with 28.8 g (0.12 mole) of ethyl $\beta,\beta,\beta$-trimethoxypropionate (for 80 % pure). The excess of acetic acid and propionate was removed by evaporation at 100°–110°C under reduced pressure of 1 mm Hg. 11.4 g (0.1 mole) of 2,2,2-trifluoroethylhydrazine (prepared according to the British Pat. No. 1,069,532 and 1 ml of acetic acid were added to the residue. Stirring was continued for 15 min. at 100°–110°C and the reaction mixture became solid. It was recrystallized from 200 ml of ethanol.

Yield : 34.6 g (62.5 %). Melting point : 201°C.

Preparation 2

Colour coupler 2 of table II 37.3 g (0.1 mole) of amine (2) in 100 ml of acetic acid were allowed to react as described in preparation 1 with 0.12 mole of ethyl $\beta,\beta,\beta$-trimethoxypropionate.

After evaporation, 12.2 g (0.1 mole) of benzylehydrazine and 1 ml of acetic acid were added. The mixture was stirred for 2½ hours at 100°–110°C and then concentrated by evaporation. The residue was recrystallized from 160 ml of methanol.

Yield : 23.5 g (43 %). Melting point : 193°C.

Preparation 3

Colour coupler 8 of table II

This coupler was prepared from 39.1 g (0.1 mole) of amine (5), 100 ml of acetic acid, 0.12 mole of ethyl $\beta,\beta,\beta$-trimethoxypropionate and 11.4 g (0.1 mole) of 2,2,2-trifluoroethylhydrazine according to the procedure of preparation 2. The recrystallization solvent was isopropylether.

Yield : 34 g (61.2 %). Melting point : 167°C.

Preparation 4

Colour coupler 9 of table II

This coupler was prepared from 32.1 g (0.1 mole) of amine (3), 100 ml of acetic acid, 0.12 mole of ethyl $\beta,\beta,\beta$-trimethoxypropionate and 19 g (0.1 mole) of $\alpha$-trifluoromethyl benzylhydrazine (prepared as described in British Pat. No. 1,069,532) following the procedure of preparation 2. The recrystallization solvent was benzene.

Yield : 38 g (67.5 %). Melting point : 149°C.

Preparation 5

Colour coupler 10 of table II

This coupler was prepared from 39.55 g (0.1 mole) of amine (7), 100 ml of acetic acid, 0.12 mole of ethyl $\beta,\beta,\beta$-trimethoxypropionate, and 11.4 g (0.1 mole) of 2,2,2-trifluoroethylhydrazine following the procedure of preparation 2. The recrystallization solvent was isopropyl ether.

Yield : 27 g (48.5 %). Melting point : 139°–141°C.

Preparation 6

Colour coupler 13 of table II

This coupler was prepared from 45.9 g (0.1 mole) of amine (9), 100 ml of acetic acid, 0.12 mole of ethyl $\beta,\beta,\beta$-trimethoxypropionate, and 13.4 g (0.11 mole) of benzylhydrazine. The residue was recrystallized from methanol and then from ethanol.

Yield : 19 g (30 %). Melting point : 89°C.

Preparation 7

Colour coupler 18 of table II 24.9 g (0.1 mole) of amine (6), 28.8 g (0.12 mole) of ethyl $\beta,\beta,\beta$-trimethoxypropionate and 2 ml of acetic acid were heated for 3 hours at 80°C. The excess of acetic acid and propionate was removed by evaporation at 100–110°C under reduced pressure of 1 mm Hg.

39.6 g (0.1 mole) of p-n-hexadecylsulphonylphenylhydrazine, 150 ml of acetonitrile, and 2ml of acetic acid were added to the residue. The mixture was heated until complete dissolution and then left standing at room-temperature. The precipitate formed was filtered off by suction and recrystallized, first from isopropyl ether and then from acetonitrile.

Yield : 20.5 g (30 %). Melting point : 74°C.

Preparation 8

Colour coupler 21 of table II 38.9 g (0.1 mole of amine (1) and 0.12 mole of ethyl $\beta,\beta,\beta$-trimethoxy propionate were allowed to react in acetic acid as described in preparation 1.

After evaporation, 0.1 mole of 2,4-dimethyl-6-chlorophenyl hydrazine and 10 ml of acetic acid were added to the residue. The reaction mixture was stirred at 80°C for 1 hour and then suddenly became solid. It was treated with hot acetonitrile.

Yield : 36.6 g (60 %). Melting point : 226°C.

Preparation 9

Colour coupler 25 of table II

This coupler was prepared from 40.3 g (0.1 mole) of amine (4), 0.12 mole of ethyl $\beta,\beta,\beta$-trimethoxypropionate, 2 ml of acetic acid and 21.15 g (0.1 mole) of 2,4,5-trichlorophenyl hydrazine following the procedure of preparation 7.

However, the reaction mixture was left standing overnight and cyclisation was effected by addition of 50 ml of 0.2 N sodium methylate in methanol and heating for 2 hours at 50°C. After acidification with acetic acid and dilution with water, the mixture was extracted with methylene chloride. The residue obtained upon evaporation was treated with methanol.

Yield : 34 g (51 %). Melting point : 136°C.

Preparation 10

Colour coupler 26 of table II

This colour coupler was prepared from 40.3 g (0.1 mole) of amine (4), 0.12 mole of ethyl $\beta,\beta,\beta$-trimethoxypropionate, 2 ml of acetic acid and 17.7 g (0.1 mole) of 3,4-dichloro-phenylhydrazine according to the procedure of preparation 7. The recrystallization solvent was ethylene glycol monomethyl ether.

Yield : 15.5 g (25 %). Melting point : 148°C.

PREPARATION 11

Colour coupler 32 of table II 38.9 g (0.1 mole) of amine (10) and 0.12 mole of ethyl $\beta,\beta,\beta$-triemethoxypropionate were allowed to react in acetic acid as described in preparation 1.

After evaporation, 16.5 g (0.1 mole) of benzothiazolyl-hydrazine and 100 ml of acetic acid were added to the residue. The reaction mixture was heated at 60°–70°C so that first a solution and then after about 30 min. a precipitate formed. After having kept the mixture for 2 hours at 60°–70°C the precipitate was filtered off by suction and treated with methanol.

Yield: 32.5 g (50%). Melting point: 234°C.

Table II

| Colour coupler | Substituent in 1-position | | 3-position derived from | Melting point °C | Yield % |
|---|---|---|---|---|---|
| 1 | —CH₂CF₃ | | amine 1 | 201 | 62.5 |
| 2 | —CH₂—C₆H₅ | | amine 2 | 193 | 43 |
| 3 | —CH₂—C₆H₅ | | amine 1 | 173 | 50.2 |
| 4 | —CH₂—C₆H₅ | | amine 3 | 208 | 48 |
| 5 | —CH₂CF₃ | | amine 3 | 188–190 | 47.5 |
| 6 | —CH₂CF₃ | | amine 2 | 238 | 48.5 |
| 7 | —CH₂CF₃ | | amine 4 | 185 | 60 |
| 8 | —CH₂CF₃ | | amine 5 | 167 | 61.2 |
| 9 | C₆H₅—CH—CF₃ | | amine 3 | 149 | 67.5 |
| 10 | —CH₂CF₃ | | amine 7 | 139–141 | 48.5 |
| 11 | —CH₂CF₃ | | amine 8 | 150 | 57.5 |
| 12 | —CH₂CF₃ | | amine 9 | 110 | 46.5 |
| 13 | —CH₂C₆H₅ | | amine 9 | 89 | 30 |
| 14 | C₆H₅—CH—CF₃ | | amine 8 | 200 | 34.5 |
| 15 | —CH₂CF₃ | | amine 10 | 228 | 61 |
| 16 | —CH₂C₆H₅ | | amine 10 | 235 | 60 |
| 17 | C₆H₅—CH—CF₃ | | amine 10 | 258 | 64 |
| 18 |  | —SO₂—(CH₂)₁₅—CH₃ | amine 6 | 74 | 26 |
| 19 |  | —SO₂N(CH₂)₁₅CH₃ / CH₃ | amine 6 | 149 | 27.7 |
| 20 |  | —SO₂—(CH₂)₁₅—CH₃ | amine 3 | 163 | 43 |
| 21 |  | —CH₃ | amine 1 | 226 | 60 |
| 22 |  | —Cl | amine 1 | 208 | 60 |
| 23 |  | —Cl | amine 1 | 236 | 29.1 |
| 24 |  | —Cl | amine 2 | 140 | 38 |
| 25 |  | —Cl | amine 4 | 136 | 51 |
| 26 |  | —Cl | amine 4 | 148 | 25 |
| 27 |  | —Cl | amine 9 | 120 | 25 |
| 28 |  | —Cl | amine 9 | 160 | 12 |
| 29 |  | —Cl | amine 10 | above 240 | 49 |

Table II-continued

| Colour coupler | Substituent in 1-position | Substituent in 3-position derived from | Melting point °C | Yield % |
|---|---|---|---|---|
| 30 | 2,6-dichloro-4-methylphenyl | amine 10 | above 240 | 44.5 |
| 31 | benzothiazol-2-yl | amine 10 | 238 | 30 |
| 32 | benzothiazol-2-yl | amine 10 | 234 | 30 |

The non-diffusible colour couplers according to the present invention can be incorporated into the photographic silver halide element according to any suitable technique known in the art. The colour couplers of the invention are preferably incorporated into photographic hydrophillic colloid media from solutions in high boiling sparingly water-miscible solvents such as di-n-butyl phthalate and tricresyl phosphate or in low-boiling sparingly water-miscible solvents such as ethyl acetate, methylene chloride, diethyl carbonate, chloroform, etc. or mixtures thereof in that they have a high solubility therein and very fine dispersions can be obtained by means of these solvents.

For this purpose these solutions can be dispersed in extremely fine droplets, preferably in the presence of one or more wetting or dispersing agents into a hydrophilic colloid medium e.g. aqueous gelatin or into water, the low-boiling sparingly water-miscible solvent then being removed by evaporation. The stable dispersions of the colour couplers can be stored as such and then admixed whenever desired with coating composition itself of the hydrophilic colloid layer such as a silver halide emulsion layer into which the compounds are intended to be present.

Of course the compounds of the invention can also be incorporated into the hydrophilic colloid media in other ways.

More details about particularly suitable techniques that may be employed for incorporating the colour couplers of the invention into a hydrophilic colloid layer of a photographic material there can be referred to e.g. U.S. Pat. Nos. 2,269,158 — 2,284,887 — 2,304,939 — 2,304,940 and 2,322,027, United Kingdom Pat. Specifications No. 791,219 — 1,098,594 — 1,099,414 — 1,099,415 — 1,099,416 — 1,099,417 — 1,218,190 — 1,272,561 and 1,297,347, French Pat. No. 1,555,663, Belgian Pat. No. 722,026, German Pat. No. 1,127,714 and to United Kingdom Pat. Specification No. 1,297,947.

The couplers according to the invention may be used in conjunction with various kinds of photographic emulsions. Various silver salts may be used as the sensitive salt such as silver bromide, silver iodide, silver chloride or mixed silver halides such as silver chlorobromide, silver bromoiodide and silver chlorobromoiodide. The couplers can be used in emulsions of the mixed packet type as described in U.S. Pat. No. 2,698,794 or emulsions of the mixed grain type as described in U.S. Pat. No. 2,592,243. The colour couplers can be used with emulsions wherein latent images are formed predominantly on the surface of the silver halide crystal, or with emulsions wherein latent images are formed predominantly inside the silver halide crystal.

The hydrophilic colloid used as the vehicle for the silver halide may be, for example, gelatin, colloidal, albumin, zein, casein, a cellulose derivative, a synthetic hydrophilic colloid such as polyvinyl alcohol, poly-N-vinyl pyrrolidone, etc. If desired, compatible mixtures of two or more of these colloids may be employed for dispersing the silver halide.

The light-sensitive silver halide emulsions of use in the preparation of a photographic material according to the present invention may be chemically as well as optically sensitized. They may be chemically sensitized by effecting the ripening in the presence of small amounts of sulphur containing compounds such as allyl thiocyanate, allyl thiourea, sodium thiosulphate, etc. The emulsions may also be sensitized by means of reductors for instance tin compounds as described in French Pat. No. 1,146,955 and in Belgian Pat. No. 568,687, imino-amino methane sulphinic acid compounds as described in United Kingdom Pat. Specification No. 789,823 and small amounts of noble metal compounds such as gold, platinum, palladium, iridium, ruthenium and rhodium compounds. They may be optically sensitized by means of cyanine and merocyanine dyes.

The said emulsions may also comprise compounds which sensitize the emulsions by development acceleration for example compounds of the polyoxyalkylene type such as alkylene oxide condensation products as described among others in U.S. Pat. No. 2,531,832 — 2,533,990 — 3,210,191 and 3,158,484, in United Kingdom Pat. Specifications No. 920,637 and 991,608 and in Belgian Pat. No. 648,710 and onium derivatives of amino-N-oxides as described in United Kingdom Pat. Specification No. 1,121,696.

Further, the emulsions may comprise stabilizers e.g. heterocyclic nitrogen-containing thioxo compounds such as benzothiazoline-2-thione and 1-phenyl-2-tetrazoline-5-thione and compounds of the hydroxytriazolopyrimidine type. They can also be stabilized with mercury compounds such as the mercury compounds described in Belgian Pat. No. 524,121 — 677,337 and 707,386 and in U.S. Pat. No. 3,179,520.

The light-sensitive emulsions may also comprise all other kinds of ingredients such as plasticizers, hardening agents, wetting agents, etc.

The non-diffusing magenta colour formers described in the present invention are usually incorporated into the greensensitized silver halide emulsion for forming one of the differently sensitized silver halide emulsion layers of a photographic multilayer colour material. Such photographic multilayer colour material usually comprises a support, a red-sensitized silver halide emulsion layer with a cyan colour former, a green-sensitized silver halide emulsion layer with a magenta colour former and a blue-sensitive silver halide emulsion layer with a yellow colour former.

The emulsions can be coated on a wide variety of photographic emulsion supports. Typical supports include cellulose ester film polyvinylacetal film, polystyrene film polyethylene terephthalate film and related films or resinous materials, as well as paper and glass. It is also possible to employ paper coated with α-olefin polymers e.g. paper coated with polyethylene, polypropylene, ethylene-butylene copolymers, etc.

For the production of photographic colour images according to the present invention an exposed silver halide emulsion layer is developed with an aromatic primary amino developing substance in the presence of a colour coupler according to the present invention. All colour developing agents capable of forming azomethine dyes can be utilised as developers. Suitable developing agents are aromatic compounds such as p-phenylene diamine and derivatives for example, N,N-diethyl-p-phenylene diamine, N-butyl-N-sulphobutyl-p-phenylene diamine, N,N-diethyl-N'-sulphomethyl-p-phenylene diamine, N,N-diethyl-N'-carboxymethyl-p-phenylene diamine, 2-amino-5-diethylaminotoluene, 4-amino-N-ethyl-N(β-methanesulphonamidoethyl)-m-toluidine, N-hydroxyethyl-N-ethyl-p-phenyle diamine, etc.

The following examples illustrate the present invention.

EXAMPLE 1

An aqueous gelatin dispersion of 16 g of colour coupler 18 having the following structural formula

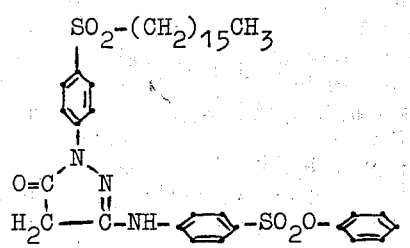

was admixed with 500 g of a green-sensitized silver bromoiodide (3 mole % of iodide) emulsion containing 0.115 mole of silver halide.

The aqueous gelatin dispersion was prepared by dispersing with the help of an ultrasonic wave generator a solution of 6 g of colour coupler in 30 ml. of ethyl acetate in 100 ml of a 5 % aqueous solution of gelatin containing 1.5 g of the sodium salt of lauryl benzene sulphonate and then removing the ethyl acetate by evaporation under reduced pressure.

After neutralization of the emulsion and addition of the common additives such as stabilizers, wetting agents and hardeners, the emulsion was coated on a cellulose triacetate support, dried and overcoated with a gelatin antistress layer.

The material was exposed for 1/20 sec. through a grey wedge with constant 0.15 and developed for 8 min. at 20°C in a developing bath of the following composition:

| | |
|---|---|
| 2-amino-5-diethylaminotoluene HCl | 2.5 g |
| anhydrous sodium sulphite | 5 g |
| anhydrous sodium carbonate | 20 g |
| potassium bromide | 2 g |
| water to make | 1 liter. |

The silver image and residual silver halide were removed by treatment in a potassium hexacyanoferrate (III) bleach and a sodium thiosulphate fixer.

A magenta coloured wedge was obtained having absorption maximum at 556 nm.

EXAMPLE 2

Another sample of the material prepared as described in example 1 was exposed and processed in the same way with the difference that the developer had the following composition:

| | |
|---|---|
| 2-amino-5-[N-ethyl-N(β-methylsulphonyl-amino)ethyl]aminotoluene sulphate | 2 g |
| anhydrous sodium sulphite | 0.5 g |
| anhydrous sodium carbonate | 30 g |
| water to make | 1 liter |

A magenta coloured wedge was obtained having absorption maximum at 556 nm.

EXAMPLE 3

Examples 1 and 2 were repeated with the only difference that now colour coupler 18 was replaced by colour coupler 19 of the following structural formula:

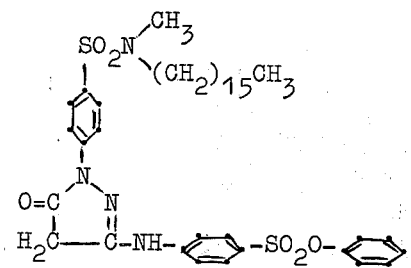

Magenta wedge images were obtained having absorption maxima at 548 nm (developer of example 1) and 546 nm (developer of example 2).

EXAMPLE 4

Examples 1 and 2 were repeated with the only difference that colour coupler 18 was replaced by colour coupler 20 of the following structural formula:

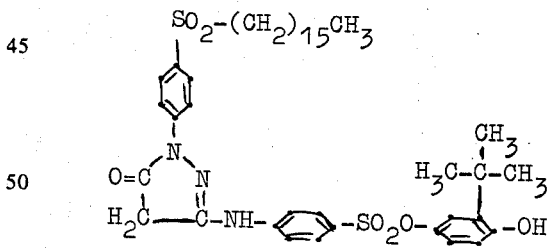

Magenta wedge images were obtained having absorption maxima at 556 nm (developer of example 1) and 558 nm (developer of example 2).

We claim:

1. Method of producing a magenta coloured photographic image in a photographic light-sensitive silver halide material which comprises exposing the material and developing it with an aromatic primary amino colour developing agent in the presence of a 3-anilino-2-pyrazolin-5-one colour coupler wherein the anilino group carries an aryloxysulphonyl group.

2. Method according to claim 1, wherein the 2-pyrazolin-5-one colour coupler corresponds to the formula:

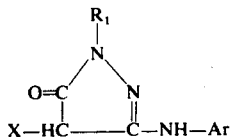

wherein:
R₁ represents an alkyl group, an aryl group, or a heterocycle,
X represents hydrogen or a substituent that exhibits 2-equivalent character,
Ar represents a phenyl group carrying an aryloxysulphonyl group.

3. Method according to claim 1 wherein the aryloxysulphonyl group is a phenyloxysulphonyl group which may be substituted with one or more of the groups alkyl, cycloalkyl, hydroxy, halogen, alkoxy, alkylthio or alkylsulphonyl.

4. Method according to claim 2 wherein in the formula the group Ar represents a group of the formula:

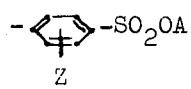

wherein:
Z is hydrogen, halogen, alkoxy, or alkylthio, and
A is a carbocyclic aryl group which may be substituted with one or more of the groups, alkyl, cycloalkyl, hydroxy, halogen, alkoxy, alkylthio or alkylsulphonyl.

5. A photographic element containing at least one silver halide emulsion layer and a 3-anilino-2-pyrazolin-5-one compound wherein the anilino group carries an aryloxy sulphonyl group.

6. A photographic element according to claim 5 wherein the compound corresponds to the formula:

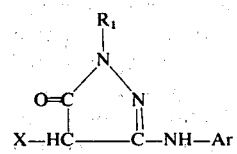

wherein:
R₁ represents an alkyl group, an aryl group, or a heterocycle,
X represents hydrogen or a substituent that exhibits 2-equivalent character,
Ar represents a phenyl group carrying an aryloxysulphonyl group.

7. A photographic element according to claim 5 wherein the aryloxysulphonyl group is a phenyloxysulphonyl group which may be substituted with one or more of the groups alkyl, cycloalkyl, hydroxy, halogen, alkoxy, alkylthio or alkylsulphonyl.

8. A photographic element according to claim 6 wherein in the formula the group Ar represents a group of the formula:

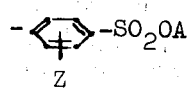

wherein:
Z is hydrogen, halogen, alkoxy, or alkylthio, and
A is a carbocyclic aryl group which may be substituted with one or more of the groups, alkyl, cycloalkyl, hydroxy, halogen, alkoxy, alkylthio or alkylsulphonyl.

9. A photographic element according to claim 5, wherein the aryloxysulphonyl group comprises one or more aliphatic hydrocarbon groups of at least 5 C-atoms.

10. A photographic element according to claim 5 wherein said 3-anilino-2-pyrazolin-5-one compound carries in the 1-position an aryl group containing an aliphatic hydrocarbon group of at least 5 carbon atoms.

* * * * *